United States Patent
Van Der Schaaf et al.

(10) Patent No.: US 7,045,661 B2
(45) Date of Patent: May 16, 2006

(54) CRYSTALLINE FORMS OF VENLAFAXINE HYDROCHLORIDE

(75) Inventors: Paul Adriaan Van Der Schaaf, Allschwil (CH); Claudia Marcolli, Zürich (CH); Martin Szelagiewicz, Münchenstein (CH); Beat Freiermuth, Buschwiller (FR)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 11/093,484

(22) Filed: Mar. 30, 2005

(65) Prior Publication Data

US 2005/0256205 A1 Nov. 17, 2005

Related U.S. Application Data

(62) Division of application No. 10/130,042, filed as application No. PCT/EP01/12240 on Oct. 23, 2001, now Pat. No. 6,906,087.

(30) Foreign Application Priority Data

Oct. 31, 2000 (EP) .................................. 00811014

(51) Int. Cl.
*C07C 211/00* (2006.01)

(52) U.S. Cl. ...................................................... 564/336
(58) Field of Classification Search ................. 564/336
See application file for complete search history.

(56) References Cited

U.S. PATENT DOCUMENTS

| 5,043,466 A | 8/1991 | Shepard ...................... 558/371 |
| 2002/0143211 A1 | 10/2002 | Dolitzky et al. ............ 564/316 |
| 2002/0183553 A1 | 12/2002 | Dolitzky et al. ............ 564/316 |
| 2003/0105359 A1 | 6/2003 | Van Der Schaaf et al. . 564/339 |
| 2003/0109585 A1 | 6/2003 | Ali et al. .................... 514/649 |

FOREIGN PATENT DOCUMENTS

| EP | 0112669 | 7/1984 |
| EP | 0444855 | 9/1991 |
| WO | 02/45658 | 6/2002 |
| WO | 02/46140 | 6/2002 |

OTHER PUBLICATIONS

J. Yardley et al., J. Med. Chem. (1990), vol. 33, pp. 2899-2905.

*Primary Examiner*—Samuel Barts
(74) *Attorney, Agent, or Firm*—Kevin T. Mansfield

(57) ABSTRACT

Crystalline forms of Venlafaxine hydrochloride were found, referred to hereinafter as polymorphic Forms A, B and D. Furthermore, the present invention is directed to processes for the preparation of these crystalline forms and pharmaceutical compositions comprising the crystalline forms.

9 Claims, 6 Drawing Sheets

CRYSTALLINE FORMS OF VENLAFAXINE HYDROCHLORIDE

This application is a divisional of application Ser. No. 10/130,042, filed on Oct. 1, 2002, now U.S. Pat. No. 6,906,087 which is the National Stage of International Application PCT/EP01/12240, filed Oct. 23, 2001.

The present invention is directed to crystalline forms of Venlafaxine hydrochloride, processes for their preparation and pharmaceutical compositions comprising these crystalline forms.

The present invention relates to crystalline forms of Venlafaxine hydrochloride. Venlafaxine hydrochloride is known by the chemical name 1-[(2-dimethylamino)-1-(4-methoxyphenyl)ethyl]cyclohexanol hydrochloride. Venlafaxine hydrochloride has the following formula:

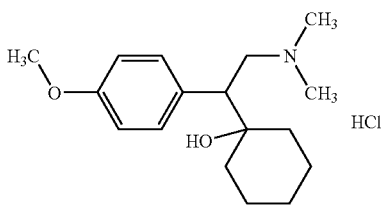

Venlafaxine is an anti-depressant and acts by inhibiting synaptosomal uptake of norepinephrine (3H—NE) and serotonin (14C-5HT). Processes for the preparation of Venlafaxine hydrochloride are described in EP-A-112,669 and in Yardley et al., J. Med. Chem., 1990, vol. 33, page 2899. This hydrochloride salt is desirable since it enables Venlafaxine to be conveniently formulated. There is still a need to produce Venlafaxine in a reproducible, pure and crystalline form to enable formulations to meet exacting pharmaceutical requirements and specifications. Furthermore, it is economically desirable that the product is stable for extended periods of time without the need for specialised storage conditions. The processes in the above mentioned patent and publication result in the preparation of a crystalline form of Venlafaxine hydrochloride having a melting point between 215 and 217° C. which is herein designated as Form C. Surprisingly, there have now been found several novel crystalline forms of Venlafaxine hydrochloride, herein designated as Form A and B, and a new crystalline hydrate of Venlafaxine hydrochloride, herein designated as Form D. The novel forms of the present invention have a good thermal stability and/or good solubility characterisitics. An additional advantage of Form B is that this form is thermodynamically more stable than the previous known Form C.

Accordingly, the present invention is directed to the following polymorphic Forms A, B and D of Venlafaxine hydrochloride:

A crystalline polymorph of 1-[(2-dimethylamino)-1-(4-methoxyphenyl)ethyl]cyclohexanol hydrochloride which exhibits a characteristic X-ray powder diffraction pattern with characteristic peaks expressed in d-values (Å) at 15.3 (vw), 11.9 (w), 9.6 (w), 9.1 (vw), 8.1 (vw), 7.7 (w), 6.3 (vw), 6.0 (m), 5.92 (m), 5.46 (vw), 5.20 (m), 5.00 (w), 4.91 (vw), 4.77 (m), 4.57 (s), 4.49 (s), 4.31 (s), 4.26 (s), 4.04 (vw), 3.98 (vw), 3.90 (vw), 3.82 (w), 3.68 (vw), 3.60 (w), 3.52 (w), 3.45 (vw), 3.33 (m), 3.29 (m), 3.22 (vw), 3.15 (vw), 3.07 (vw), 2.87 (vw), 2.81 (w), 2.72 (vw), 2.58 (vw), 2.51 (vw), 2.49 (vw), 2.43 (vw), 2.35 (vw);

herein designated as Form A. Here and in the following the abbreviations in brackets mean:

(vs)=very strong intensity; (s)=strong intensity; (m)=medium intensity; (w)=weak intensity; (vw)=very weak intensity; and (sh)=shoulder.

A crystalline polymorph of 1-[(2-dimethylamino)-1-(4-methoxyphenyl)ethyl]cyclohexanol hydrochloride which has characteristic Raman bands, expressed in wave number ($cm^{-1}$):

3075 (m), 3059 (m), 3014 (s), 3000 (m), 2938 (vs), 2915 (s), 2900 (sh), 2863 (m), 2835 (m), 1613 (s), 1583 (w), 1464 (m), 1447 (m), 1273 (m), 1238 (m), 1201 (s), 1181 (s), 1142 (m), 1084 (w), 1062 (w), 1045 (m), 984 (m), 974 (m), 961 (w), 863 (m), 849 (s), 839 (s), 818 (s), 739 (m), 722 (m), 662 (w), 636 (m), 498 (w), 454 (w), 417 (m), 372 (w), 221 (m);

herein designated as Form A.

A crystalline polymorph of 1-[(2-dimethylamino)-1-(4-methoxyphenyl)ethyl]cyclohexanol hydrochloride which exhibits a characteristic X-ray powder diffraction pattern with characteristic peaks expressed in d-values (Å) at 13.0 (w), 8.6 (s), 6.5 (m), 5.86 (w), 5.71 (s), 5.34 (vw), 5.22 (vw), 5.11 (vw), 4.85 (m), 4.48 (m), 4.36 (vs), 4.08 (s), 3.90 (m), 3.70 (vw), 3.50 (vw), 3.47 (w), 3.35 (vw), 3.27 (w), 3.23 (vw), 3.16 (w), 3.10 (vw), 3.04 (vw), 3.00 (vw), 2.86 (w), 2.83 (vw), 2.76 (vw), 2.73 (vw), 2.71 (vw), 2.62 (vw), 2.55 (m), 2;48 (vw), 2.43 (vw), 2.39 (vw), 2.34 (vw);

herein designated as Form B.

A crystalline polymorph of 1-[(2-dimethylamino)-1-(4-methoxyphenyl)ethyl]cyclohexanol hydrochloride which exhibits a characteristic X-ray powder diffraction pattern with characteristic peaks expressed in d-values (Å) at 11.7 (s), 10.2 (w), 7.7 (vw), 6.8 (m), 5.90 (vs), 5.67 (w), 5.57 (vw), 5.37 (m), 5.04 (w), 4.91 (vw), 4.76 (m), 4.70 (m), 4.53 (w), 4.47 (w), 4.42 (vw), 4.32 (m), 4.14 (m), 4.10 (w), 3.95 (vw), 3.84 (w), 3.77 (vw), 3.68 (w), 3.60 (vw), 3.50 (w), 3.35 (m), 3.28 (w), 3.15 (w), 3.07 (vw), 3.04 (vw), 3.01 (vw), 2.93 (w), 2.84 (w), 2.77 (vw), 2.72 (w), 2.68 (vw), 2.63 (w), 2.59 (w), 2.46 (vw), 2.37 (vw), 2.35 (vw), 2.31 (vw), 2.27 (vw), 2.26 (vw);

herein designated as Form D.

A crystalline polymorph of 1-[(2-dimethylamino)-1-(4-methoxyphenyl)ethyl]cyclohexanol hydrochloride which has characteristic Raman bands, expressed in wave number ($cm^{-1}$):

3082 (w), 3058 (m), 3022 (m), 2998 (w), 2972 (m), 2953 (s), 2938 (vs), 2916 (m), 2899 (m), 2865 (m), 2856 (m), 2835 (m), 1616 (vs),91584 (w), 1472 (m), 1452 (m), 1440 (m), 1322 (w), 1303 (w), 1268 (m), 1254 (w), 1241 (w), 1202 (m), 1182 (s), 1143 (w), 1078 (w), 1062 (w), 1044 (w), 980 (m), 973 (w), 862 (w), 848 (s), 840 (s), 817 (vs), 738 (w), 723 (w), 661 (w), 637 (m), 417 (m), 375 (w), 277 (w), 224 (m), 178 (w);

herein designated as Form D.

Known Form C exhibits a characteristic X-ray powder diffraction pattern with characteristic peaks expressed in d-values (Å) at 12.9 (w), 10.5 (w), 8.6 (vw), 6.9 (s), 6.5 (m), 5.66 (w), 5.52 (w), 5.41 (m), 5.25 (w), 5.10 (w), 4.67 (s), 4.47 (w), 4.34 (vs), 4.18 (vs), 4.07 (m), 3.99 (vw), 3.87 (vw), 3.69 (vw), 3.55 (m), 3.51 (vw), 3.46 (w), 3.39 (w), 3.32 (vw), 3.26 (w), 3.12 (m), 3.09 (w), 2.94 (vw), 2.88 (w), 2.83 (m), 2.75 (vw), 2.73 (vw), 2.69 (w), 2.64 (m), 2.55 (m), 2.48 (vw), 2.46 (vw), 2.43 (vw), 2.38 (w), 2.35 (vw), 2.32 (w), 2.30 (w), 2.26 (vw).

A discussion of the theory of X-ray powder diffraction patterns can be found in "X-ray diffraction procedures" by H. P. Klug and L. E. Alexander, J. Wiley, New York (1974).

Furthermore, the present invention is directed to processes for the preparation of Forms A, B and D. In addition, the present invention is directed to processes for the preparation of highly pure crystalline Form B. Highly pure Form B is to be understood having a content of this form of 95% by weight, especially 97.5% by weight and preferably 99% by weight.

Form A can be prepared by heating Form C to a temperature just above its melting point (for example 1 to 20° C., especially 1 to 10° C. above its melting point) in order to form crystals of Form A.

Form B can be prepared by equilibrating a slurry of polymorphic Form C in an organic solvent, preferably an alcoholic or ketone solvent, especially isopropanol, and separating Form B. The process can be performed with or without the addition of seeding crystals. The addition of seeding crystals is preferred.

Alternatively, Form B can be prepared by dissolving Venlafaxine hydrochloride in an organic solvent, preferably isopropanol, at elevated temperature (for example 40 to 80° C., especially 50 to 70° C.) and subsequent cooling. It is preferred to cool to room temperature. The concentration of Venlafaxine hydrochloride is for example 5 to 20% by weight, especially 10 to 15% by weight. The cooling rate can vary and is for example 0.1 to 2° C. per minute, especially 0.1 to 0.5° C. per minute. Preferably, seeding crystals of Form B are added, especially within the metastable zone width, for example at 1 to 10° C., especially 1 to 3° C. below the temperature of complete dissolution. The quantity of added seeding crystals is for example 2 to 10% and especially 10% of the quantity of Venlafaxine hydrochloride. The seeding crystals are preferably ground before the addition.

Form D can be prepared by evaporating an aqueous solution of Venlafaxine hydrochloride. Preferably evaporation is carried out at a temperature of 10 to 60° C., most preferably at 20 to 40° C., especially at room temperature. It is preferred to carry out evaporation in air.

The preparation of crystalline polymorphic Forms A, B and D is usually carried out by using Form C as the starting compound.

Form C can, for example, be obtained by preparing a solution of Venlafaxine hydrochloride in isopropanol at elevated temperature (for example 40 to 80° C., especially 50 to 70° C.) and subsequent cooling of the solution (for example to 0 to 20° C., especially to about 0° C.). Precipitated Form C can then be separated.

Another object of the present invention are pharmaceutical compositions comprising an effective amount of crystalline polymorphic Form A, B or D, and a pharmaceutically acceptable carrier.

The polymorphic forms may be used as single components or mixtures.

As to pharmaceutical compositions of Venlafaxine hydrochloride it is preferred that these contain 25–100% by weight, especially 50–100% by weight, of at least one of the novel forms, based on the total amount of Venlafaxine hydrochloride. Preferably, such an amount of the novel polymorphic forms of Venlafaxine hydrochloride is 75–100% by weight, especially 90–100% by weight. Highly preferred is an amount of 95–100% by weight.

The following Examples illustrate the invention in more detail. Temperatures are given in degrees Celsius, parts and percentages are by weight, unless otherwise stated.

EXAMPLE 1

Preparation of Polymorphic Form C 100 parts of Venlafaxine hydrochloride are dissolved in 1600 parts of isopropanol at a temperature of 60° C. and subsequently cooled to a temperature of 0° C. This leads to the precipitation of Form C. X-ray powder diffraction studies show the product to be polymorphic Form C (see FIG. 1).

EXAMPLE 2

Preparation of Polymorphic Form A

Form C of Venlafaxine hydrochloride is heated just above its melting point. Newly formed crystals of Form A start to grow out of this melt. X-ray powder diffraction studies show the product to be polymorphic Form A (see FIG. 2). A Raman spectrum of Form A is given in FIG. 3.

EXAMPLE 3

Preparation of Polymorphic Form B

A slurry of 100 parts of Form C of Venlafaxine hydrochloride in 800 parts of isopropanol is equilibrated for 3 days. Subsequent filtration and drying gives pure Venlafaxine hydrochloride Form B. X-ray powder diffraction studies show the product to be polymorphic Form B (see FIG. 4).

EXAMPLE 4

Preparation of Polymorphic Form D 80 parts of Form C of Venlafaxine hydrochloride are dissolved in 500 parts of water. The solution is evaporated in air at room temperature. This gives Venlafaxine hydrochloride Form D. X-ray powder diffraction studies show the product to be polymorphic Form D (see FIG. 5). A Raman spectrum of Form D is given in FIG. 6.

EXAMPLE 5

Preparation of Polymorphic Form B 100 parts of Form C of Venlafaxine hydrochloride are dissolved in 800 parts of isopropanol at 70° C. At 63° C. 10 parts of ground Form B of Venlafaxine hydrochloride are added as seeding crystals. The temperature is lowered with a cooling rate of 0.1° C. per minute to room temperature. Subsequent filtration and drying gives pure Venlafaxine hydrochloride Form B.

Figure 1:
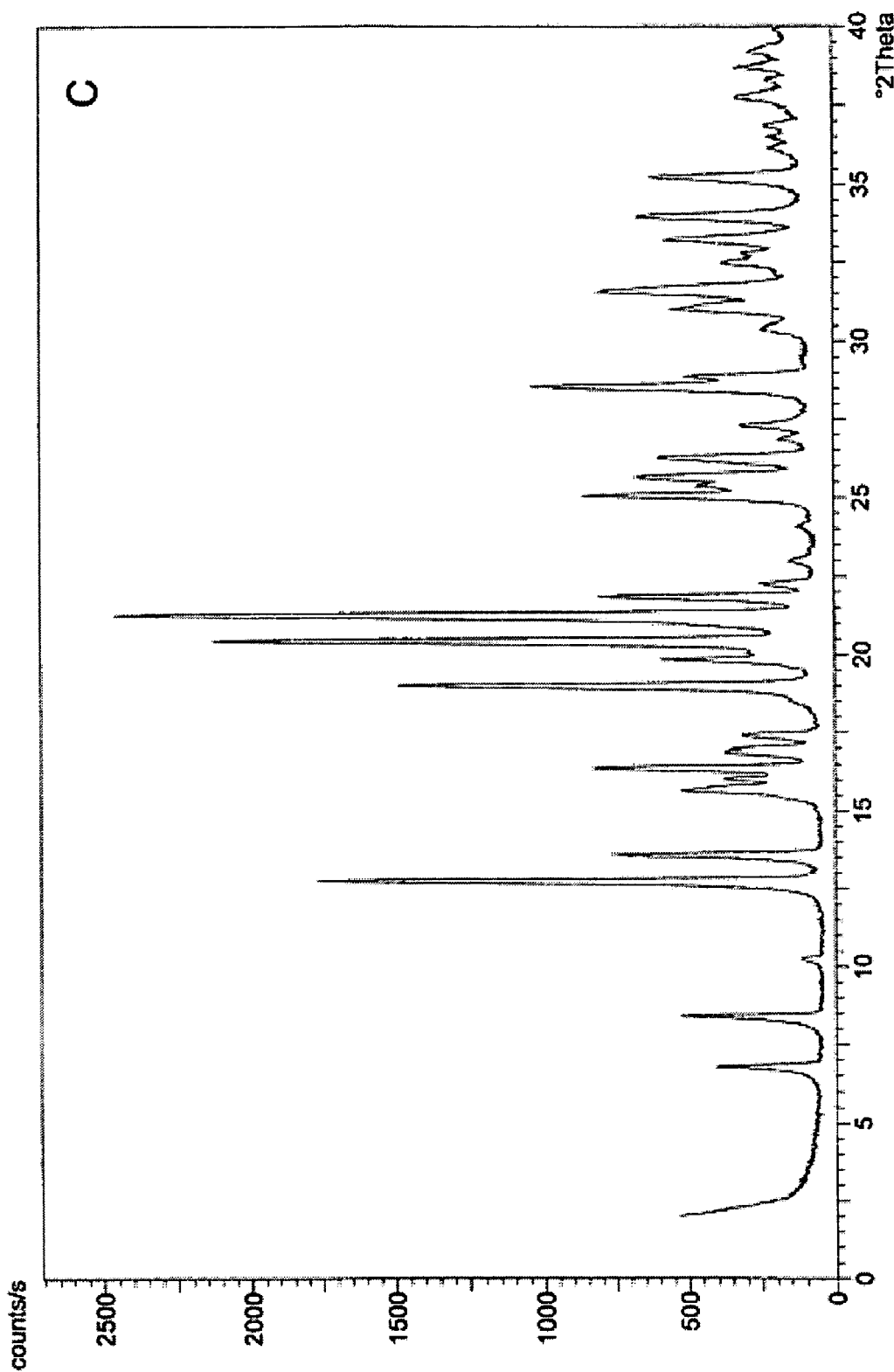
FIG. 1 is a characteristic X-ray powder diffraction pattern for Form C
Figure 2:
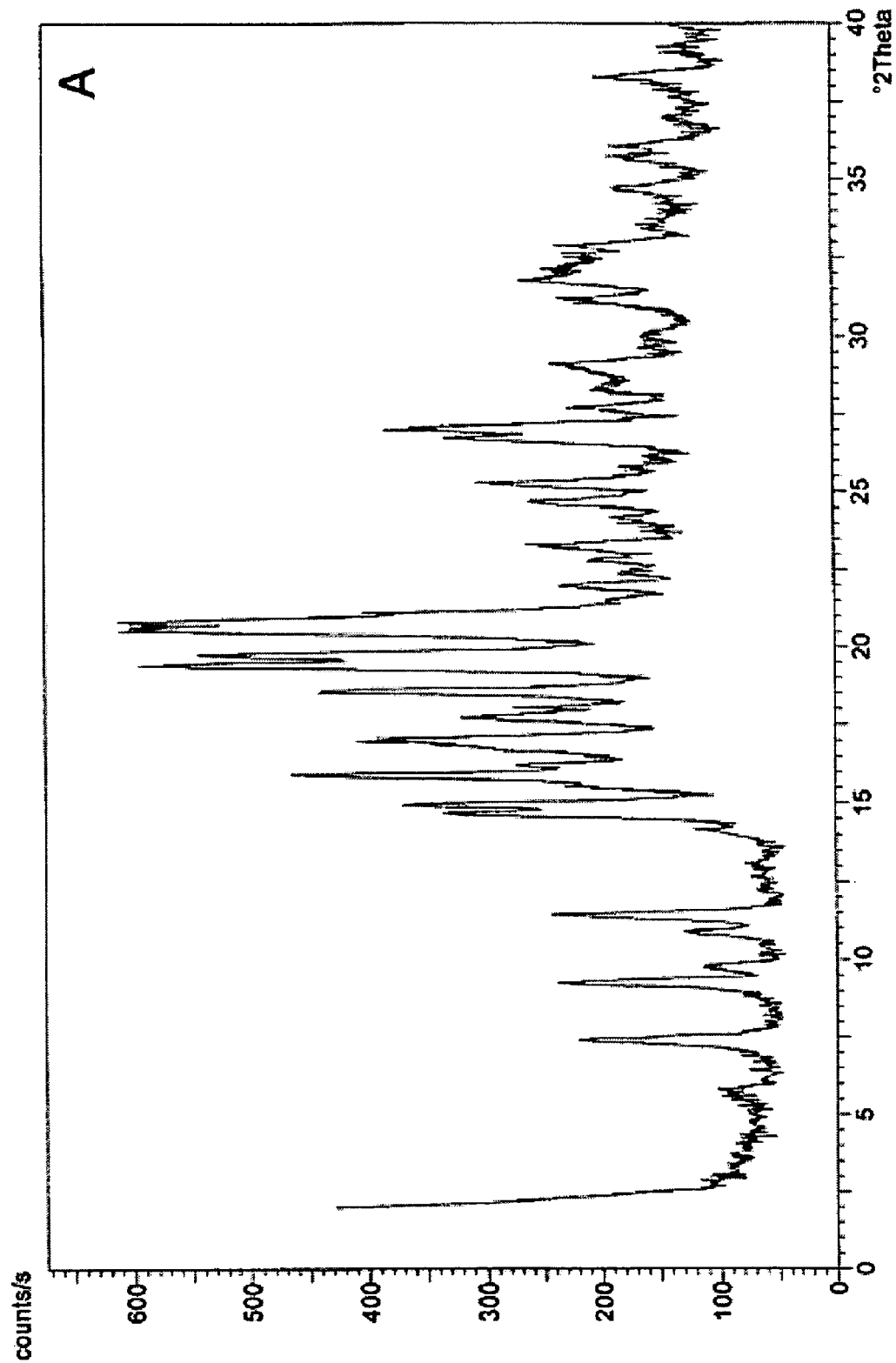
FIG. 2 is a characteristic X-ray powder diffraction pattern for Form A
Figure 3:
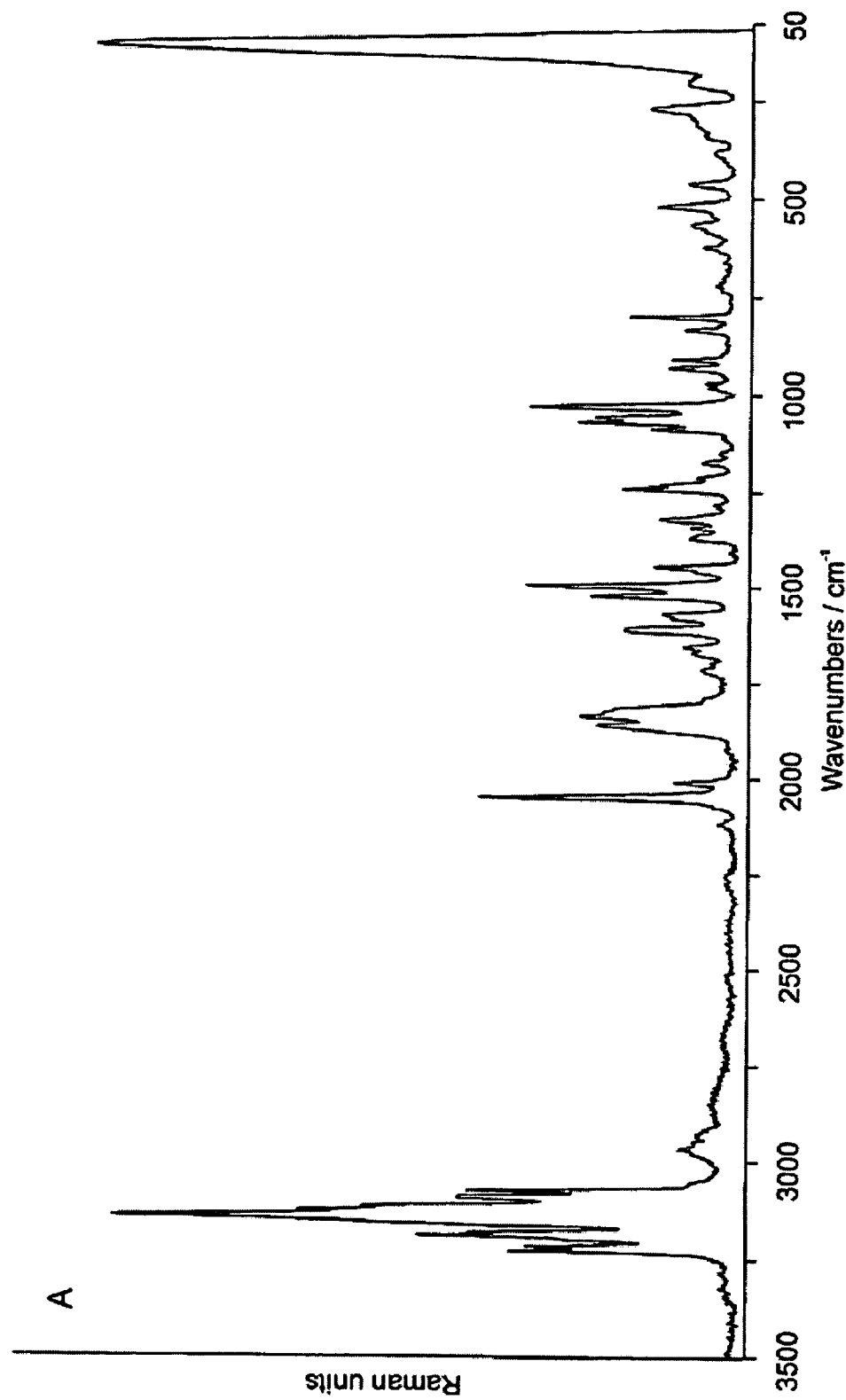
FIG. 3 is a characteristic Raman spectrum of Form A
Figure 4:
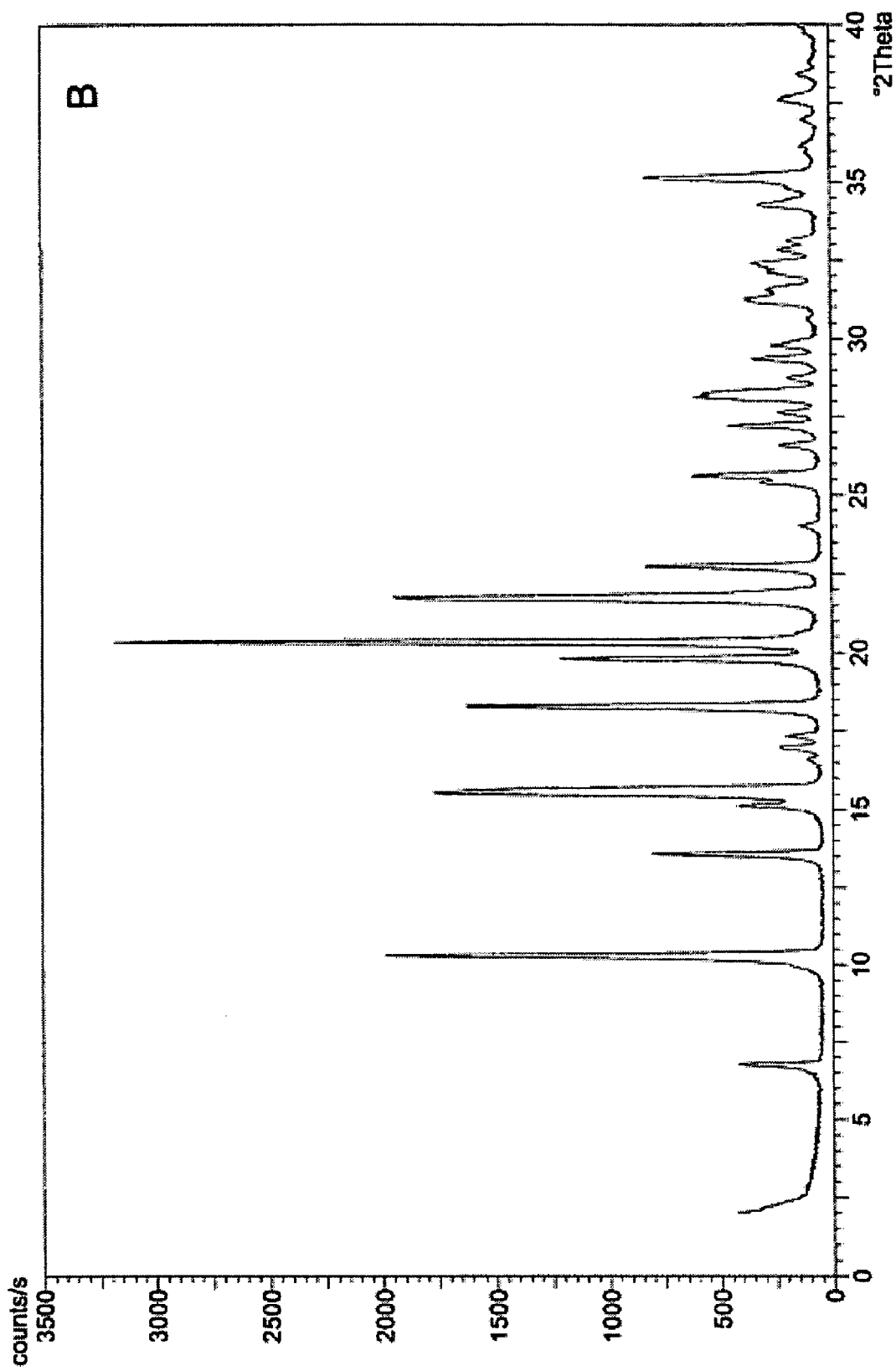
FIG. 4 is a characteristic X-ray powder diffraction pattern for Form B
Figure 5:
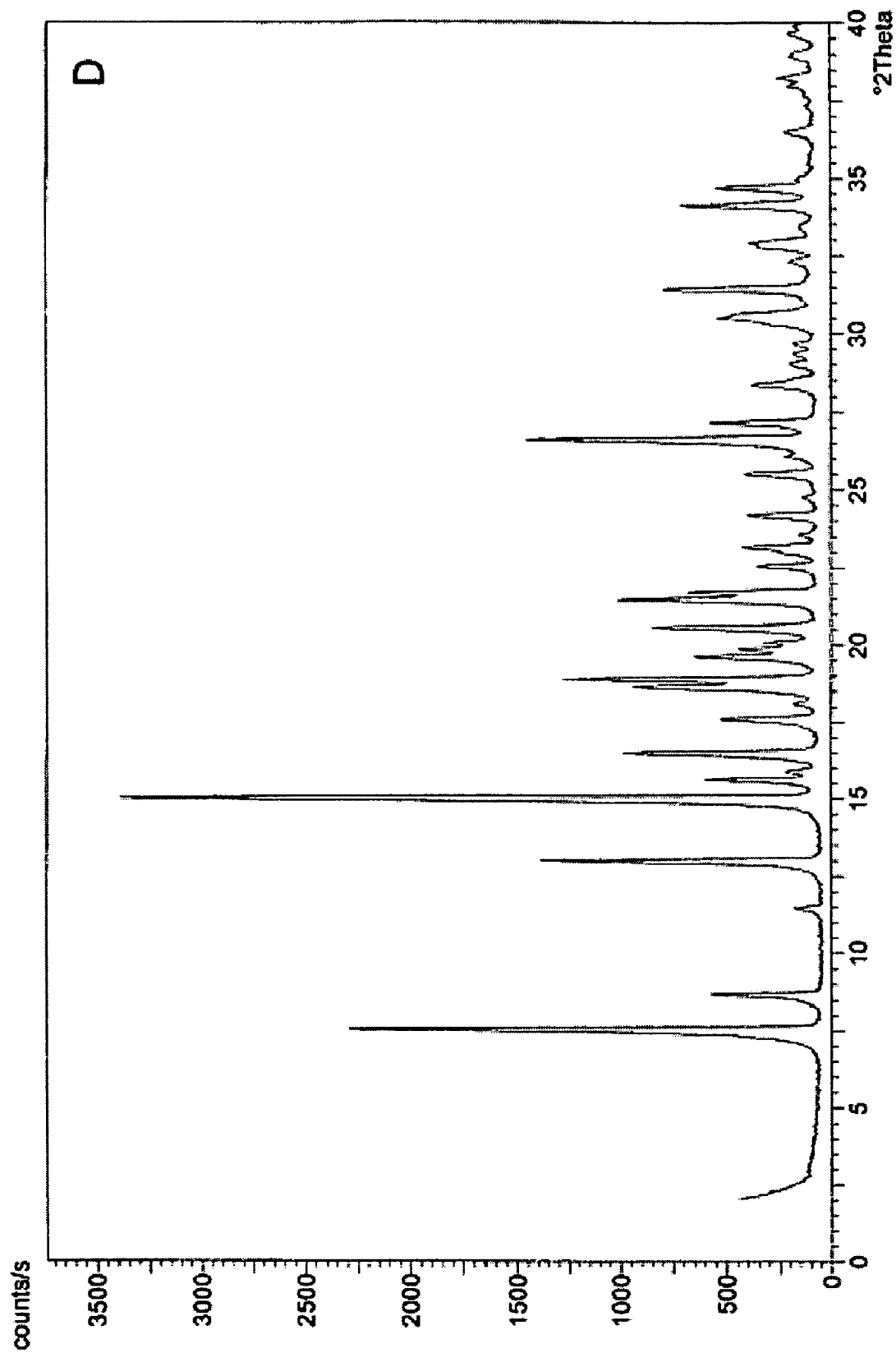
FIG. 5 is a characteristic X-ray powder diffraction pattern for Form D
Figure 6:
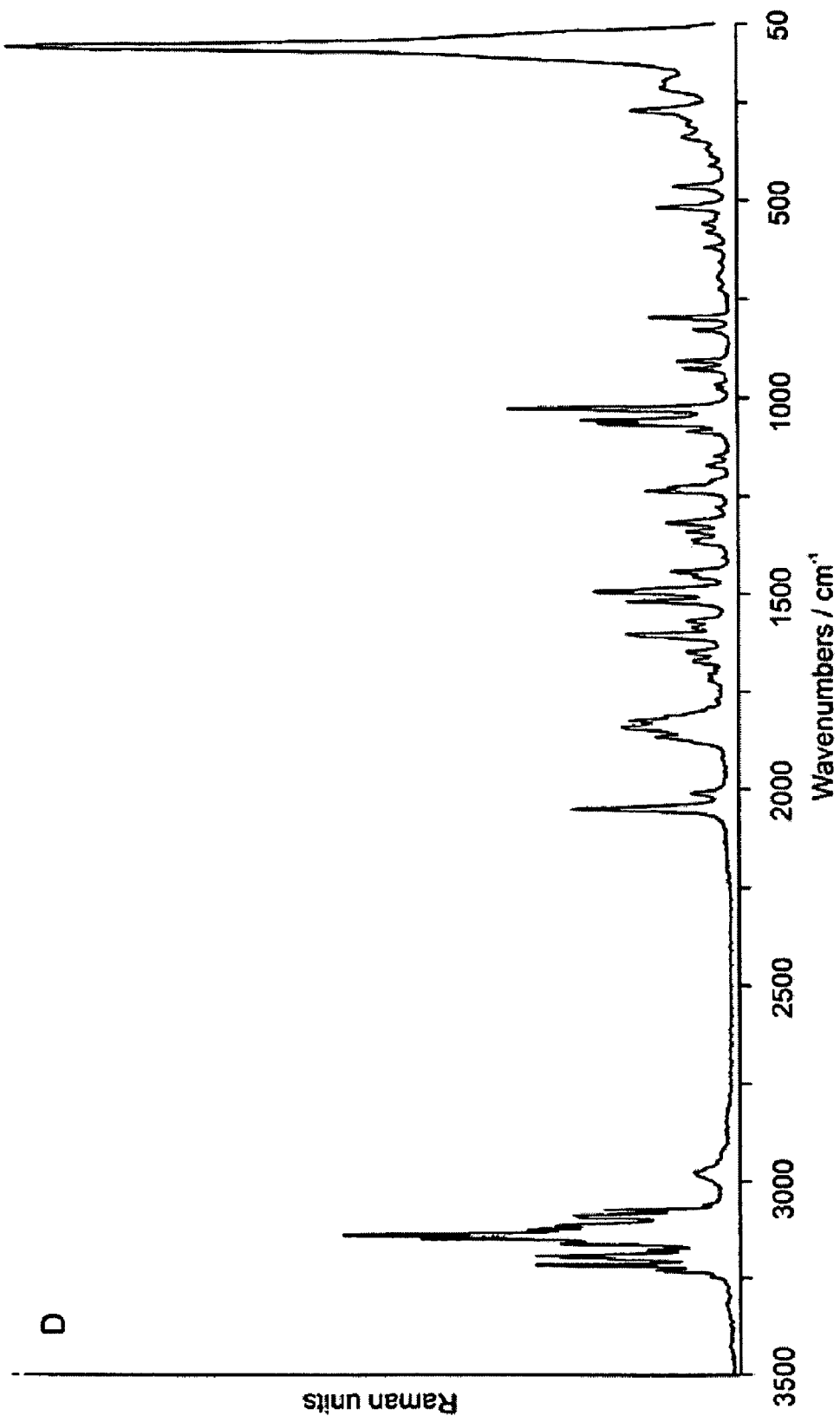
FIG. 6 is a characteristic Raman spectrum of Form D

The invention claimed is:

1. A process for the preparation of a crystalline polymorph of 1-[(2-dimethylamino)-1-(4-methoxyphenyl)ethyl]cyclohexanol hydrochloride which exhibits a characteristic X-ray powder diffraction pattern with characteristic peaks expressed in d-values (Å) at 15.3 (vw), 11.9 (w), 9.6 (w), 9.1 (vw), 8.1 (vw), 7.7 (w), 6.3 (vw), 6.0 (m), 5.92 (m), 5.55 (m), 5.46 (vw), 5.20 (m), 5.00 (w), 4.91 (vw), 4.77 (m), 4.57 (s), 4.49 (s), 4.31 (s), 4.26 (s), 4.04 (vw), 3.98 (vw), 3.90 (vw), 3.82 (w), 3.68 (vw), 3.60 (w), 3.52 (w), 3.45 (vw), 3.33 (m), 3.29 (m), 3.22 (vw), 3.15 (vw), 3.07 (vw), 2.87 (vw), 2.81 (w), 2.72 (vw), 2.58 (vw), 2.51 (vw), 2.49 (vw), 2.43 (vw), 2.35 (vw):

wherein (s)=strong intensity; (m)=medium intensity; (w)=weak intensity; and (vw)=very weak intensity, which comprises dissolving Venlafaxine in an organic solvent to form a solution at elevated temperature, adding seeding crystals, cooling the solution, and separating the crystalline polymorph.

2. A process according to claim 1, wherein the seeding crystals are ground before addition to the solution.

3. A process for the preparation of the crystalline polymorph defined in claim 1, which comprises equilibrating a slurry of polymorphic Form C in isopropanol and separating the crystalline polymorph defined in claim 1.

4. A process for the preparation of a crystalline polymorph of 1-[(2-dimethylamino)-1-(4-methoxyphenyl)ethyl]cyclohexanol hydrochloride which exhibits a characteristic X-ray powder diffraction pattern with characteristic peaks expressed in d-values (Å) at 11.7 (s), 10.2 (w), 7.7 (vw), 6.8 (m), 5.90 (vs), 5.67 (w), 5.57 (vw), 5.37 (m), 5.04 (w), 4.91 (vw), 4.76 (m), 4.70 (m), 4.53 (w), 4.47 (w), 4.42 (vw), 4.32 (m), 4.14 (m), 4.10 (w), 3.95 (vw), 3.84 (w), 3.77 (vw), 3.68 (w), 3.60 (vw), 3.50 (w), 3.35 (m), 3.28 (w), 3.15 (w), 3.07 (vw), 3.04 (vw), 3.01 (vw), 2.93 (w), 2.84 (w), 2.77 (vw), 2.72 (w), 2.68 (vw), 2.63 (w), 2.59 (w), 2.46 (vw), 2.37 (vw), 2.35 (vw), 2.31 (vw), 2.27 (vw), 2.26 (vw);

wherein (vs)=very strong intensity; (s)=strong intensity; (m)=medium intensity; (w)=weak intensity; and (vw)=very weak intensity, which comprises evaporating or lyophilisation of an aqueous solution of 1-[(2-dimethylamino)-1-(4-methoxyphenyl)ethyl]cyclohexanol hydrochloride.

5. A process according to claim 1, wherein the organic solvent is isopropanol.

6. A process according to claim 1, wherein the quantity of seeding crystals is 2 to 10% of the quantity of Venlafaxine hydrochloride.

7. A process according to claim 1, wherein the seeding crystals are added within a metastable zone 1 to 10° C. below the temperature of complete dissolution.

8. A process according to claim 1, wherein the elevated temperature is 40 to 80° C.

9. A process according to claim 1, wherein cooling rate is 0.1 to 2° C. per minute.

* * * * *